US00PP13711P29

(12) United States Plant Patent
Hofmann

(10) Patent No.: US PP13,711 P2
(45) Date of Patent: Apr. 8, 2003

(54) NEW GUINEA IMPATIENS PLANT NAMED 'FISIMP 149'

(76) Inventor: Birgit Hofmann, Gassenweg 29, 56170 Bendorf (DE)

( * ) Notice: Subject to any disclaimer, the term of this patent is extended or adjusted under 35 U.S.C. 154(b) by 0 days.

(21) Appl. No.: 10/080,595

(22) Filed: Feb. 22, 2002

(51) Int. Cl.[7] ..... A01H 5/00
(52) U.S. Cl. ..... Plt./318
(58) Field of Search ..... Plt./318

*Primary Examiner*—Bruce R. Campell
*Assistant Examiner*—Susan B. McCormick
(74) *Attorney, Agent, or Firm*—C A Whealy

(57) ABSTRACT

A new and distinct cultivar of New Guinea Impatiens plant named 'Fisimp 149', characterized by its outwardly spreading, rounded and uniformly mounded plant habit; freely branching and freely flowering habit; large rounded dark pink-colored flowers with red purple-colored eye that are positioned above and beyond the foliage; and leaves with dark green-colored upper surfaces, dark red-colored lower surfaces, and red-colored petioles and venation.

1 Drawing Sheet

BOTANICAL CLASSIFICATION/CULTIVAR DESIGNATION

*Impatiens hawkeri* cultivar Fisimp 149.

BACKGROUND OF THE INVENTION

The present Invention relates to a new and distinct cultivar of New Guinea Impatiens plant, botanically known as *Impatiens hawkeri,* and hereinafter referred to by the name 'Fisimp 149'.

The new Impatiens is a product of a planned breeding program conducted by the Inventor in Hillscheid, Germany. The objective of the breeding program is to develop new moderately compact Impatiens cultivars that flower relatively early with large rounded flowers and attractive flower colors.

The new Impatiens originated from a cross made by the Inventor in July, 1998 of the *Impatiens hawkeri* cultivar Neptis, disclosed in U.S. Plant Pat. No. 10,321, as the female, or seed, parent with the *Impatiens hawkeri* cultivar Woya, disclosed in U.S. Plant Pat. No. 10,858, as the male, or pollen, parent. The cultivar Fisimp 149 was discovered and selected by the Inventor as a flowering plant within the progeny of the stated cross in a controlled environment in Moncarapacho, Portugal in March, 1999.

Asexual reproduction of the new cultivar by terminal cuttings taken in Moncarapacho, Portugal, since March, 1999, has shown that the unique features of this new Impatiens are stable and reproduced true to type in successive generations.

SUMMARY OF THE INVENTION

The following traits have been repeatedly observed and are determined to be the unique characteristics of 'Fisimp 149'. These characteristics in combination distinguish 'Fisimp 149' as a new and distinct Impatiens cultivar:

1. Outwardly spreading, rounded and uniformly mounded plant habit.
2. Freely branching and freely flowering habit.
3. Large rounded dark pink-colored flowers with a red purple-colored eye that are positioned above and beyond the foliage.

4. Leaves with dark green-colored upper surfaces, dark red-colored lower surfaces, and red-colored petioles and venation.

Plants of the new Impatiens can be compared to plants of the female parent, the cultivar Neptis. In side-by-side comparisons conducted by the Inventor in Hillscheid, Germany, plants of the new Impatiens differed from plants of the cultivar Neptis in the following characteristics:

1. Plants of the new Impatiens were shorter, broader and had shorter internodes than plants of the cultivar Neptis.
2. Flower color of plants of the new Impatiens was dark pink with a red purple eye whereas flower color of plants of the cultivar Neptis was light pink and red bi-colored.

Plants of the new Impatiens can be compared to plants of the male parent, the cultivar Woya. In side-by-side comparisons conducted by the Inventor in Hillscheid, Germany, plants of the new Impatiens differed from plants of the cultivar Woya in the following characteristics:

1. Plants of the new Impatiens were not as compact as plants of the cultivar Woya.
2. Flower color of plants of the new Impatiens was darker pink than flower color of plants of the cultivar Woya.

Plants of the new Impatiens and the cultivar Fisimp 130, U.S. Plant Patent application filed concurrently, differ in flower coloration.

Plants of the new Impatiens can also be compared to plants of the cultivar Grenada, disclosed in U.S. Plant Pat. No. 9,343. In side-by-side comparisons conducted by the Inventor in Hillscheid, Germany, plants of the new Impatiens differed from plants of the cultivar Grenada in the following characteristics:

1. Plants of the new Impatiens were more broad than plants of the cultivar Grenada.
2. Leaves of plants of the new Impatiens were shorter and more broad than leaves of plants of the cultivar Grenada.
3. Flowers of plants of the new Impatiens were larger, more rounded and flatter than flowers of plants of the cultivar Grenada.
4. Flowers of plants of the new Impatiens had a larger and darker red purple-colored eye than flowers of plants of the cultivar Grenada.

5. Flowers of plants of the new Impatiens were dark pink in color whereas flowers of plants of the cultivar Grenada were light red in color.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens. The photograph comprises a side perspective view of a typical flowering plant of 'Fisimp 149' grown in a container.

DETAILED BOTANICAL DESCRIPTION

The cultivar Fisimp 149 has not been observed under all possible environmental conditions. The phenotype may vary somewhat with variations in environment such as temperature and light intensity, without, however, any variance in genotype.

The aforementioned photographs, following observations and measurements describe plants grown in Langley, British Columbia, Canada, under commercial practice in a greenhouse. Rooted young plants were planted in 17.5-cm containers during the spring and the aforementioned photograph and following observations and measurements were taken during the summer about 17 weeks later. During the production of the plants, day temperatures ranged from 21 to 24° C. and night temperatures were about 17 to 18° C. In the following description, color references are made to The Royal Horticultural Society Colour Chart, 1995 Edition, except where general terms of ordinary dictionary significance are used.

Botanical classification: *Impatiens hawkeri* cultivar Fisimp 149.

Parentage:

*Female parent.*—*Impatiens hawkeri* cultivar Neptis, disclosed in U.S. Plant Pat. No. 10,321.

*Male parent.*—*Impatiens hawkeri* cultivar Woya, disclosed in U.S. Plant Pat. No. 10,858.

Propagation:

*Type cutting.*—Terminal tip cuttings.

*Time to initiate roots.*—Summer: About 8 to 9 days at 24° C. Winter: About 10 days at 21° C.

*Time to produce a rooted cutting.*—Summer: About 15 days at 24° C. Winter: About 18 days at 21° C.

*Root description.*—Numerous, fibrous, and freely branching; 159A in color.

Plant description:

*General appearance.*—Outwardly spreading, low, rounded and uniformly mounded plant growth habit; freely branching habit, dense and bushy appearance; freely flowering. Moderately vigorous.

*Crop time.*—From a rooted cutting, about 10 to 11 weeks are required to produce finished flowering plants in 12-cm containers.

*Plant height.*—About 20.8 cm.

*Plant diameter or spread.*—About 56.4 cm.

*Lateral branches.*—Quantity per plant: About 12. Length: About 17.5 cm. Diameter: About 9 mm. Internode length: About 4.5 cm. Color: Young branches, 181A; older branches mostly light green, 143C.

*Foliage description.*—Arrangement: Primarily in whorls. Length: About 15.9 cm. Width: About 5 cm. Shape: Elliptic. Apex: Acuminate. Base: Acute. Margin: Serrulate with ciliation. Texture: Smooth, slightly rugose; glabrous. Color: Young and fully expanded foliage, upper surface: 139A. Young and fully expanded foliage, lower surface: 184A. Venation, upper surface: 53C to 53D. Venation, lower surface: 53B. Petiole: Length: About 2.25 cm. Diameter: About 4.5 mm. Color: Upper surface: 53D. Lower surface: 184B.

Flower description

*Flower type and flowering habit.*—Single; large rounded dark pink-colored flowers with red purple-colored eye. Freely and continuously flowering; usually about 6 to 8 flowers and flower buds per lateral branch. Flowers flat and positioned above and beyond the foliage and typically face parallel to the leaf canopy. Petals not persistent; gynoecium persistent. Flowers not fragrant.

*Flower longevity.*—Flowers last about 8 to 9 days on the plant.

*Flowering season.*—Year-round under greenhouse conditions. Plants begin flowering about 9 to 10 weeks after planting.

*Flower buds.*—Length: About 2.1 cm. Diameter: About 1.6 cm. Shape: Ovoid. Color: 50A.

*Flower length.*—About 6.8 cm.

*Flower width.*—About 6.6 cm.

*Flower depth.*—About 7.5 mm.

*Petals.*—Quantity: Five per flower, imbricate. Length: Banner petals: About 3.1 cm. Lateral and base petals: About 3.1 cm. Width: Banner petal: About 4.8 cm. Lateral and base petals: About 3.75 cm. Shape: Roughly cordate. Apex: Retuse to emarginate; two shallow lobes. Base: Attenuate. Margin: Entire. Aspect: Mostly flat. Texture: Smooth; satiny. Color: When opening and fully opened, upper surface: Ground color, 52C; center of banner petal and fine longitudinal lines on lateral and base petals, 43B to 43C, faint. Towards base of petals or eye, close to 53A. Ground color becoming closer to 51A with subsequent development. When opening and fully opened, lower surface: 52B.

*Spur.*—Quantity: One per flower. Length: About 6.3 cm. Diameter: At apex: About 0.5 mm. At flower: About 3 mm. Aspect: Curved. Color: 53B.

*Peduncles.*—Length: About 6.5 cm. Diameter: About 2 mm. Strength: Strong, flexible. Angle: About 45° from the lateral branch. Color: 181B to 181C.

*Reproductive organs.*—Androecium: Stamen number: Five fused at anthers, hooded; filaments free. Anther length: About 6 mm. Anther shape: Obovate. Anther color: 54A. Pollen amount: Moderate. Pollen color: 8D. Gynoecium: Pistil quantity: One per flower. Pistil length: About 5 mm. Stigma color: 54A. Style color: 54A. Ovary: Five-celled. Ovary color: 185A.

*Seed/fruit.*—Seed and fruit development has not been observed.

Disease/pest resistance: Plants of the new Impatiens have not been observed to be resistant to pathogens and pests common to Impatiens.

It is claimed:

1. A new and distinct cultivar of New Guinea Impatiens plant named 'Fisimp 149', as illustrated and described.

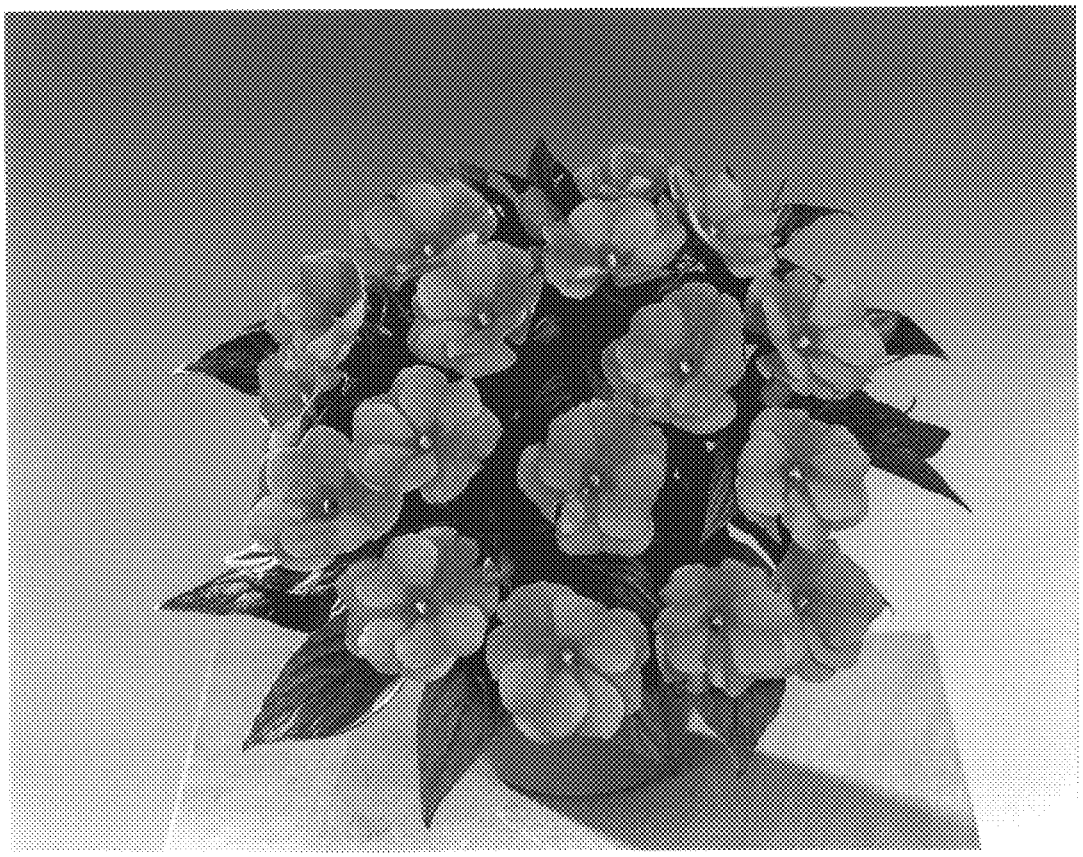

* * * * *